(12) United States Patent
Berke

(10) Patent No.: US 11,707,645 B2
(45) Date of Patent: Jul. 25, 2023

(54) MOVEMENT TRACKING DEVICES AND METHODS

(71) Applicant: RED MATTER LABS, INC., Brooklyn, NY (US)

(72) Inventor: Jordan Berke, Boynton Beach, FL (US)

(73) Assignee: RED MATTER LABS, INC., Brooklyn, NY (US)

(*) Notice: Subject to any disclaimer, the term of this patent is extended or adjusted under 35 U.S.C. 154(b) by 347 days.

(21) Appl. No.: 17/057,930

(22) PCT Filed: May 22, 2019

(86) PCT No.: PCT/US2019/033444
§ 371 (c)(1),
(2) Date: Nov. 23, 2020

(87) PCT Pub. No.: WO2019/226727
PCT Pub. Date: Nov. 28, 2019

(65) Prior Publication Data
US 2021/0205662 A1     Jul. 8, 2021

Related U.S. Application Data

(60) Provisional application No. 62/674,725, filed on May 22, 2018.

(51) Int. Cl.
*A63B 24/00* (2006.01)
*G01B 7/004* (2006.01)

(52) U.S. Cl.
CPC .... *A63B 24/0062* (2013.01); *A63B 2220/803* (2013.01); *A63B 2220/836* (2013.01); *G01B 7/004* (2013.01)

(58) Field of Classification Search
CPC .......... A63B 24/0062; A63B 2220/803; A63B 2220/836; G01B 7/004; A61B 5/1118;
(Continued)

(56) References Cited

U.S. PATENT DOCUMENTS

| 5,528,141 A | 6/1996 | Kyriakis |
| 6,154,975 A | 12/2000 | Steinich |

(Continued)

FOREIGN PATENT DOCUMENTS

| JP | 2005138833 A | 6/2005 |
| WO | 0046570 A2 | 8/2000 |

OTHER PUBLICATIONS

Search Report and the Written Opinion of the International Searching Authority of PCT/US2019/033444 dated Sep. 5, 2019.

*Primary Examiner* — Giovanni Astacio-Oquendo
(74) *Attorney, Agent, or Firm* — Eversheds Sutherland (US) LLP

(57) ABSTRACT

A movement tracking device that includes a housing, a rotatable spool secured within the housing, a rotary sensor in operable communication with the spool, and a conductive wire configured to be repeatedly unspooled from and respooled onto the rotatable spool. The conductive wire has a distal end extendable from the housing. The movement tracking device also includes a plurality of resonators and a processor in communication with the plurality of resonators and the rotary sensor. The plurality of resonators are disposed in or on the housing and positioned about the conductive wire. Each of the plurality of resonators is configured to create one or more magnetic fields through which the conductive wire extends. The processor is configured to receive information from the plurality of resonators and the rotary sensor and determine a position of the conductive wire.

17 Claims, 9 Drawing Sheets

(58) Field of Classification Search
CPC ..... A61B 5/221; A61B 5/1126; A61B 5/6844; A61B 5/1121; G08C 17/02
USPC .............................. 324/207.13, 207.11, 200
See application file for complete search history.

(56) References Cited

U.S. PATENT DOCUMENTS

| | | |
|---|---|---|
| 8,739,426 B1 | 6/2014 | Freed et al. |
| 11,429,918 B2 * | 8/2022 | Taylor .................... G06Q 10/08 |
| 2022/0054892 A1 * | 2/2022 | North ..................... A61B 5/744 |
| 2022/0062738 A1 * | 3/2022 | Neuhaus ............ A63B 21/0058 |
| 2022/0105389 A1 * | 4/2022 | Lianides ................. G06F 3/011 |
| 2022/0299542 A1 * | 9/2022 | Ramalho Ferreira ... G01P 21/00 |
| 2023/0058321 A1 * | 2/2023 | Eder .................. A63B 24/0006 |

* cited by examiner

MOVEMENT TRACKING DEVICES AND METHODS

CROSS-REFERENCE TO RELATED APPLICATIONS

This application claims priority to and the benefit of U.S. provisional patent application No. 62/674,725, filed May 22, 2018, which is incorporated by reference herein in its entirety.

TECHNICAL FIELD

The present disclosure relates generally to systems, devices, and methods for tracking movements, and more particularly to three-dimensional, real-time movement monitoring, for example, tracking the motion of a person's body (or equipment held or worn by the person) during various physical activities, including, but not limited to, weightlifting and other exercises.

BACKGROUND

Athletes and exercise enthusiasts often look for ways to improve the efficiency and effectiveness of their training and workouts, which may lead to enhanced performance, reduced injury, and improved overall fitness. Technology may aid these efforts and may involve tracking the person's movements, tracking movement of the equipment, or some combination thereof. Recently, tracking devices have become common. For example, watches, wristbands, badges, clip-ons, and other equipment generally track an individual's movement through GPS, use of the equipment, or duration of time. However, each of these conventional pieces of equipment have deficiencies in tracking movement, for example, they are incapable of precisely tracking an objects position as well as movement within an inch of the target being tracked, tracking intensity, and/or recording all of the relevant information. Conventional equipment may offer accurate tracking in one dimension, but not precise tracking in two or more dimensions.

Accordingly, there remains a need to provide devices, systems, and methods to precisely track movement in three dimensions, which are readily usable with conventional exercise equipment and other systems and industries.

SUMMARY

A movement tracking device is provided. The movement tracking device includes a housing, a rotatable spool secured within the housing, a rotary sensor in operable communication with the spool, and a conductive wire configured to be repeatedly unspooled from and respooled onto the rotatable spool. The conductive wire has a distal end extendable from the housing. The movement tracking device also includes a plurality of resonators and a processor in communication with the plurality of resonators and the rotary sensor. The plurality of resonators are disposed in or on the housing and positioned about the conductive wire. Each of the plurality of resonators is configured to create one or more magnetic fields through which the conductive wire extends. The processor is configured to receive information from the plurality of resonators and the rotary sensor and to determine a position of the conductive wire.

BRIEF DESCRIPTION OF THE DRAWINGS

The detailed description is set forth with reference to the accompanying drawings illustrating examples of the device and method, in which use of the same reference numerals indicates similar or identical items. Certain embodiments of the present devices may include elements, components, and/or configurations other than those illustrated in the drawings, and some of the elements, components, and/or configurations illustrated in the drawings may not be present in certain embodiments.

DETAILED DESCRIPTION

A movement tracking device has been developed for monitoring, storing, and reporting movement of a wire (e.g., a conductive wire) in the x, y, and z directions. The device advantageously provides precise data on movement in any three-dimensional direction, as well as precisely measuring the direction, energy, and distance of the movement. In this manner, a user beneficially may receive feedback that can be used to improve the user's performance and/or form for various exercises. For example, the device may be useful for correcting exercise form, or body positions. In other applications, the device may be used to measure and track precise location and movement of an object, such as a free weight, attached thereto.

Exercise is one application of the presently disclosed movement tracking device. However, the movement tracking device may be adapted for use in other applications, including construction, industrial equipment, fishing, robotics, and naval applications. For example, the movement tracking device may be attached to equipment or material in the field of construction, such as the wrecking ball of a crane, which may be suited for a movement tracking device to help the operator understand the exact positioning and velocity of the wrecking ball. In other instances, the movement tracking device may be used for exercising to improve an athlete's form and/or for tracking exercise intensity. In yet other instances, the movement tracking device may be used for fishing. For example, the tracking device may be helpful for a sport fisher's outriggers as the boat is dragging a line; the captain may be able to understand from the line positioning whether a catch has latched onto the line. The movement tracking device may have many other uses beyond what is described herein.

Movement Tracking Device

Figure 1:
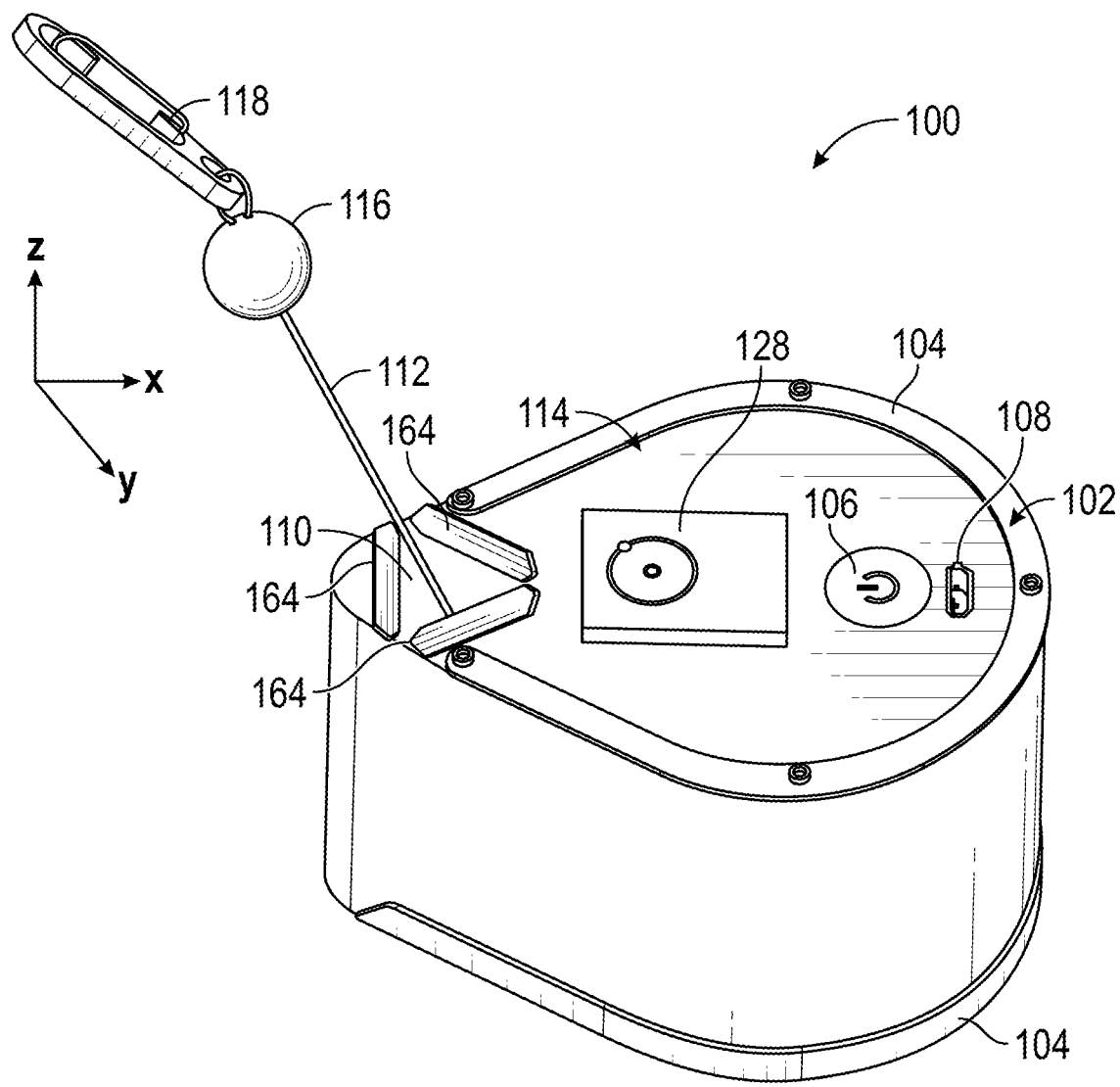
FIG. 1 is a perspective view of a movement tracking device or portion thereof according to one or more embodiments of the disclosure.
Figure 2:
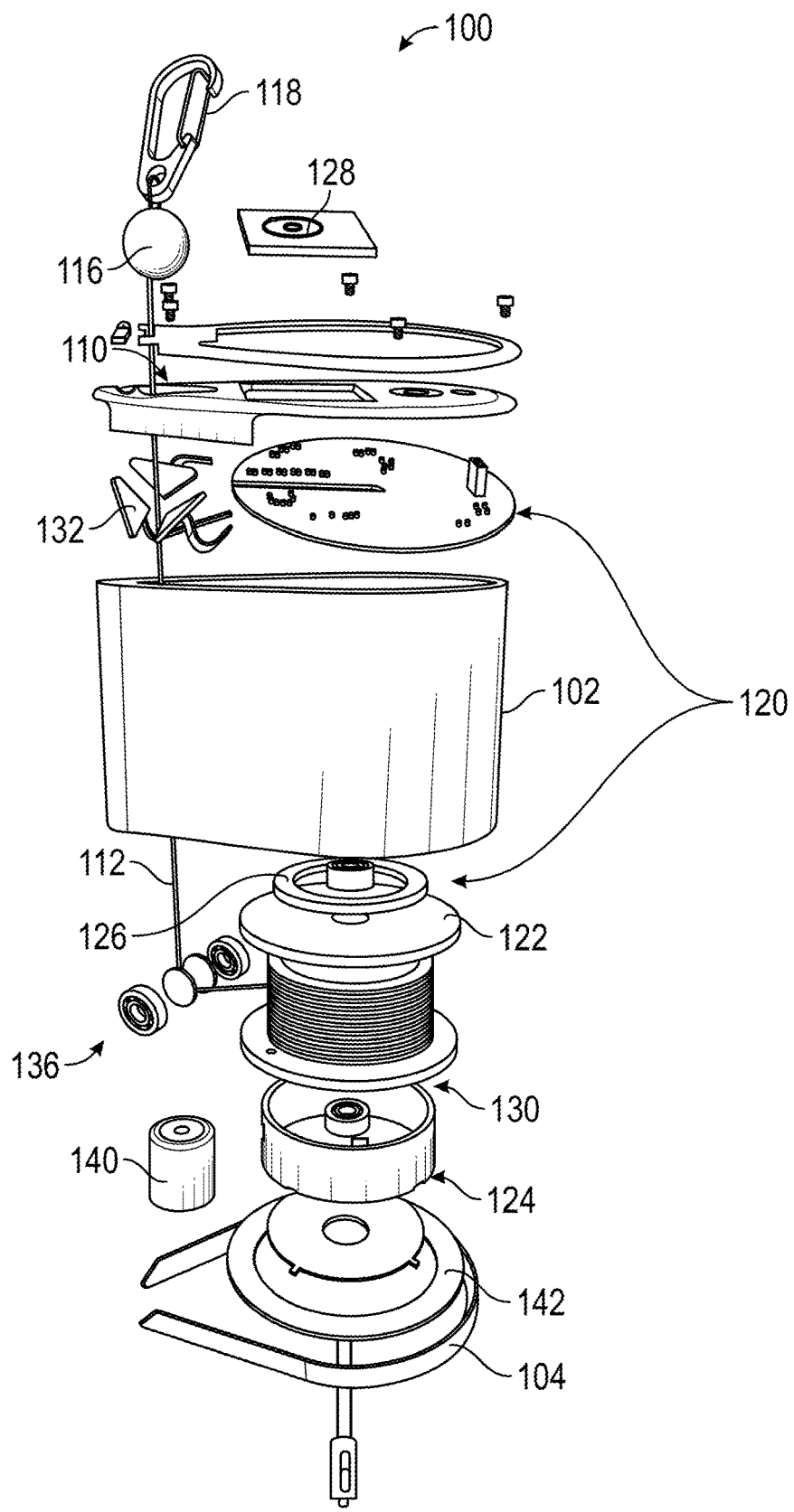
FIG. 2 is an exploded view of one embodiment of the movement tracking device according to one or more embodiments of the disclosure.

In certain embodiments, as shown in FIG. 1, a movement tracking device 100 includes a housing 102. The housing 102 is configured to protect the interior components of the movement tracking device 100, which are discussed in greater detail below. The housing 102 may be any suitable size, shape, or configuration. The housing, as shown in FIG. 2, includes a top cover that houses a power button 106, a display 128, and other components discussed below. In certain environments, the housing 102 may be subjected to harsh conditions, such as weather, sudden impact from weights, or heavy loads. Therefore, in some instances, the housing 102 may be made of a durable material, such as a metal alloy, polycarbonate, acetal copolymer polyoxymethylene, acetal homopolymer polyoxymethylene, polyethylene, polypropylene, polystyrene, polyvinyl chloride polyolefin, polyethylene terephthalate, copolymers of polypropylene, copolymers of polyethylene, EVOH, styrene, ABS, PVC, PVDC, copolymers of styrene, multilayer materials, composite materials, or bioderived materials. The housing 102 may be made of any suitable material. In some instances, the housing 102 is omitted. In such instances, the internal components of the movement tracking device 100 are incorporated into other systems or devices.

In some instances, the housing 102 includes bumpers 104 configured to absorb shock and impact forces to the movement tracking device 100. The bumpers 104 are located about the periphery of the housing 102, for example, along the edges or elsewhere. As seen in FIG. 2, the bumper 104 is on the top and the bottom of the housing 102. The bumpers 104 can be disposed about all or part of the exterior of the housing 102. The bumpers 104 may comprise rubber, silicone, gels, or plastics that provide kinetic energy distribution for the housing 102. The device may include other energy absorbing/distributing structures to facilitate device durability.

Figure 4:
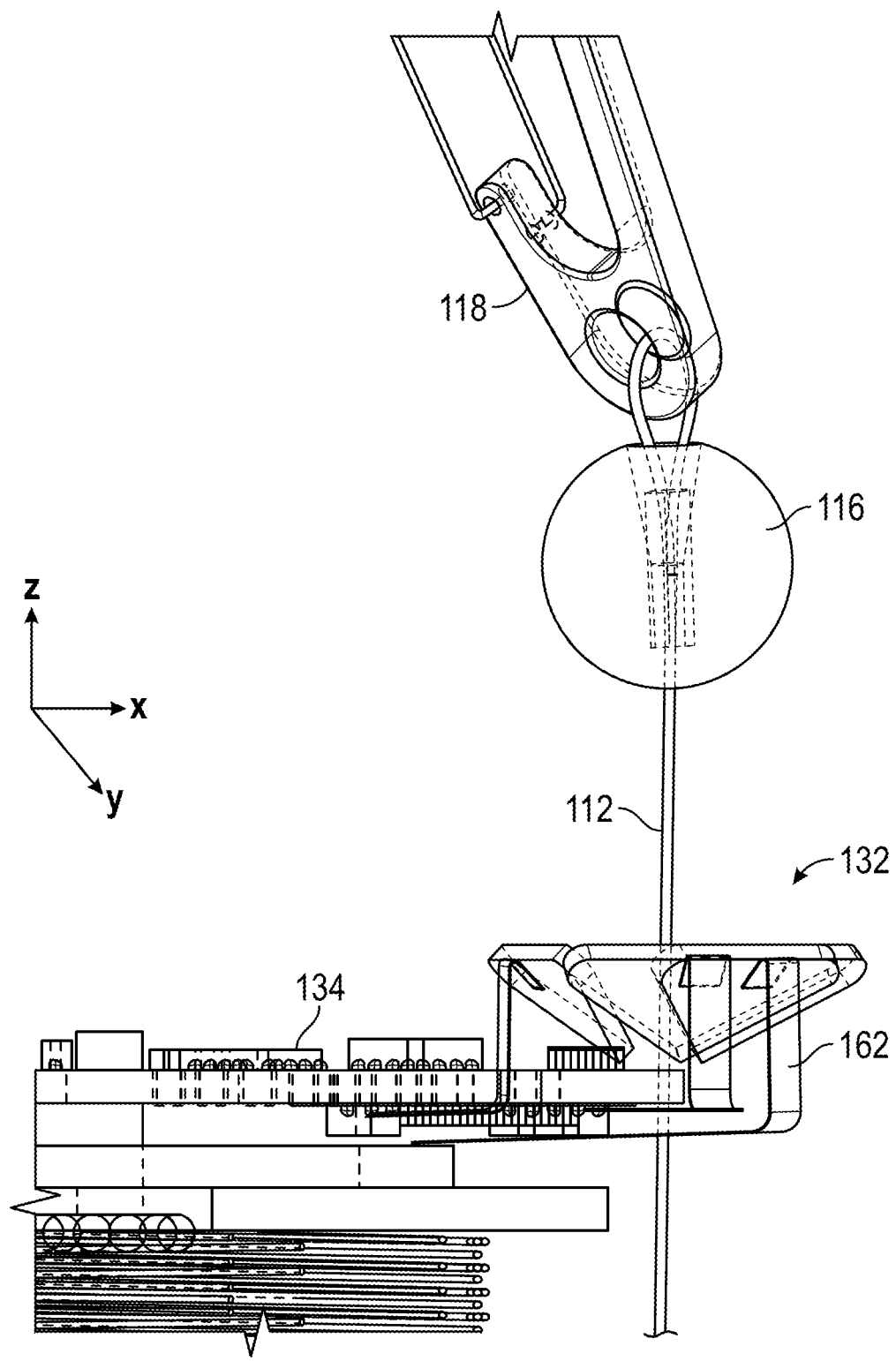
FIG. 4 is a perspective view of one embodiment of a plurality of resonators according to one or more embodiments of the disclosure.

Additionally, the housing 102, as seen in FIG. 2, includes a magnet 142 configured to mount the housing 102 to a polar exterior surface. In other instances, the housing 102 may include another method of securing to a surface, including fasteners (e.g., bolts, screws, nails, hook-and-loop, etc.), adhesive, or a combination thereof. For example, the housing 102 may include a series of apertures on the bottom of the housing to insert fasteners, which may be used to secure the housing 102 to a floor, wall, or other fixed surface. In some instances, the housing 102 is omitted and the internal components of the movement tracking device 100 are temporarily and/or permanently mounted by another method. The housing 102, as seen in FIG. 1, has sensor cavity caps 164 disposed on one side of the resonator 132 (as shown in FIG. 4) to protect the sensors from the environment and the stopper 116.

In some embodiments, the housing 102 includes a power button 106 and a charge port 108. The power button 106 is a push-button switch that is configured to complete or disconnect the circuit within the movement tracking device 100 to turn the device on and off. In other instances, the power button 106 may be a toggle switch or selector switch. The power button 106 may be any suitable switch. The charge port 108 may accept a Universal Serial Bus type A, B, or C. The charge port 108 is interconnected to an internal battery 140, as shown in FIG. 2, within the housing 102. The charge port 108 is configured to charge the internal battery 140 from a power source. The charge port 108 may be any type of port configured to work with any suitable charging cord or device. In some embodiments, the housing 102 includes a power cord that extends from the housing 102 to plug into a wall outlet.

The housing 102 has an aperture 110. In some instances, a conductive wire 112 extends through the aperture 110 from the interior of the housing 102 to the exterior of the housing 102. The aperture 110 is located on a first face 114 (e.g., an upper surface) of the housing 102. In other instances, the aperture 110 is located on a side or opposite face (e.g., bottom surface) of the housing 102. The aperture 110 may form an opening about any suitable surface of the housing 102. From the aperture 110, the conductive wire 112 can move in three dimensions. That is, the conductive wire 112 may move in the x-axis, y-axis, and/or z-axis. The x-axis extends perpendicularly to the spool 122 contained within the housing 102. The y-axis extends perpendicularly to the x-axis. The z-axis extends through the x-axis and y-axis to create an axis in three dimensions. The axes may be interchangeable and rotate in any direction relative to the housing 102. The conductive wire 112 may be coupled to a stopper 116 that prevents the conductive wire 112 from retracting fully within the housing 102. The stopper 116 also may reduce or eliminate damage on retraction of the conductive wire 112 into the housing 102. In some other embodiments, the stopper 116 is omitted. The conductive wire 112 is coupled to an attachment mechanism 118. In some instances, the attachment mechanism 118 is a clip or the like. The stopper 116 may rest on bumpers 104 located on the perimeter of the device housing 102, for example, around the aperture 110. For example, the stopper 116 may rest on the sensor cavity caps 164 placed around the aperture 110 of the device housing 102. In other instances, the stopper 116 rests partially or fully within the device housing 102.

Encoder System and Retractable Mechanism

Figure 3:
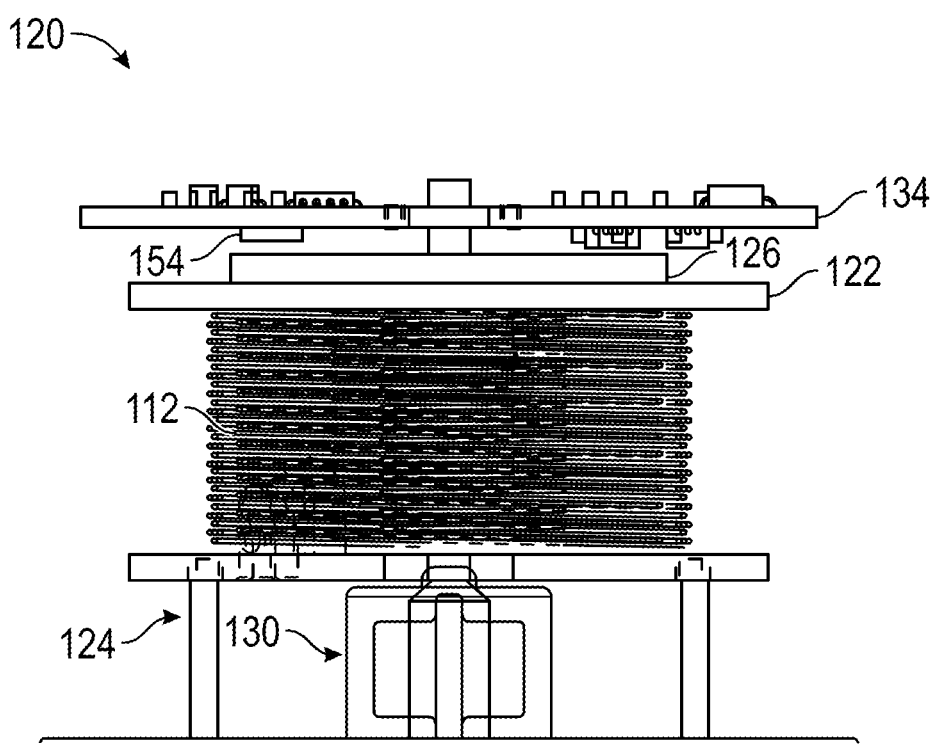
FIG. 3 is a front perspective view of one embodiment of an encoder system, a spool, a retractable mechanism, and a printed circuit board according to one or more embodiments of the disclosure.

As seen in FIGS. 2 and 3, the movement tracking device 100 includes an encoder system 120 coupled to a spool 122 and a retractable mechanism 124. The encoder system 120 is a rotary sensor. Any suitable rotary sensor may be used herein, including, but not limited to potentiometers, magnetic hall effect sensors, magneto-resistive sensors, resolvers, incremental optical encoder, absolute optical encoders, linear variable differential transformers, inductive proximity sensors, rotary encoders, and laser sensors, among others. In other instances, a linear sensor may be in communication with the conductive wire 112. That is, in some instances, the movement tracking sensor may be a rotary sensor, e.g., when the conductive wire 112 is wrapped around the spool 122, or, in other instances, the movement tracking device may be a linear sensor or the like when the conductive wire 112 is not wrapped around a spool. The movement tracking sensor may be any sensor suitable to track the movement of the conductive wire 112 along the longitudinal axis of the conductive wire 112.

The encoder system 120 includes a printed circuit board 134 (PCB), an encoder 154, and an encoder wheel 126. In some embodiments, the encoder system 120 includes an emitter (i.e., a light source for optical encoders) and a receiver (commonly referred to as an encoder). In some instances, as the spool 122 rotates, the encoder wheel 126 also rotates and measurements are taken by the encoder 154 on the PCB 134. The encoder 154 may be an optical encoder, a magnetic encoder, reflective encoder, transmissive encoder, inductive encoder, or potentiometer. The PCB 134 forms part of or is in communication with a computing device having a processor and/or memory. In some instances, the encoder wheel 126 rotates at the same rate as the spool 122. In this manner, as the spool 122 and encoder wheel 126 rotate, the encoder 154 is configured to measure the time between encoder 154 readings on the encoder wheel 126. For example, the encoder system 120 may be configured to sense a value corresponding to a specific position on the encoder wheel 126 (e.g., an absolute encoder). For example, the encoder system 120 may be configured to measure any change in position of the encoder wheel 126 (e.g., a non-absolute encoder). The processor may store the readings in a data storage device to evaluate the position of the encoder wheel 126 and send the reading to a display 128. For example, as the conductive wire 112 is pulled from the spool 122, the spool 122 and encoder wheel 126 rotate. The displacement of the conductive wire 112 is calculated by the processor correlating a known spindle diameter with a discrete change in spindle reading.

In some instances, the conductive wire 112 is wrapped around the spool 122. As the conductive wire 112 is pulled out of the aperture 110 in the housing 102, the conductive wire 112 is first pulled in a direction parallel to the conductive wire 112 direction wrapped around the spool 122. In other instances, the spool 122 has a plurality of axle bearings configured to rotate the spool 122 within the housing 102 about an axle placed within the spool 122. Next, the conductive wire 112 turns about a pulley system 136 in a perpendicular direction to the spool 122. The pulley system 136 is configured to redirect the conductive wire 112 in a variety of directions within the housing 102. The conductive wire 112 then exits the housing 102 through the aperture 110. The pulley system 136 includes at least three bearings configured to turn the wire 90 degrees. In some instances, the pulley system 136 is omitted. In such instances, the conductive wire 112 is spooled and unspooled from the spool 122 directly through the aperture 110.

The conductive wire 112 may move from the interior of the housing 102 to the exterior of the housing 102 by another method. For example, the conductive wire 112 may not be wrapped around a spool. Instead, the conductive wire 112 may be substantially linear throughout its entire movement from the interior of the housing 102 to the exterior of the housing 102. The conductive wire 112 may not be contained by a housing 102, but instead, may be configured to move in a perpendicular direction through the resonator 132. For example, the conductive wire 112 may be attached to a weight (not shown) on one end and pulled through the resonators 132. In some embodiments, the conductive wire 112 may move in a variety of other directions about the resonators 132.

In some embodiments, as seen in FIGS. 2 and 3, the spool 122 couples to a retractable mechanism 124. In some instances, the retractable mechanism 124 is a spring 130. For example, the spring 130 is at rest at a starting position of the spool 122 when the conductive wire 112 is in the retracted position within the housing 102. As the spool 122 turns, the spring 130 gathers tension and is configured to rotate the spool 122 back to the starting position once the conductive wire 112 is released. In other embodiments, the retractable mechanism 124 is another device that stores kinetic potential energy (e.g., a rubber band or the like). The retractable mechanism 124 is used in conjunction with the encoder 154 to read the movement of the conductive wire 112 in the z-axis. One benefit of the retractable mechanism 124 is that each time the conductive wire 112 is pulled from the spool 122, the conductive wire 112 automatically retracts within the housing 102. The encoder 154, as previously mentioned, is configured to read measurements of the encoder wheel 126 spinning in either direction to send information to the processor about which direction the conductive wire 112 is traveling.

Conductive Wire

As seen in FIGS. 1-8, the conductive wire 112 is configured to extend from the housing 102. The conductive wire 112 is used to measure the distance and direction of movement of the attachment mechanism 118. For example, as discussed above, the encoder system 120 is configured to measure the distance the conductive wire 112 travels in the z-direction. Similarly, as discussed in greater detail below, the conductive wire 112 disturbs a magnetic field produced by resonators 132 for positional measurements in three dimensions. The resonators 132 are in communication with the processor, which receives the information from the resonators 132 to calculate the x-axis and y-axis movement of the conductive wire 112. The conductive wire 112 may comprise copper, copper-covered steel, high strength alloy such as zirconium copper, stainless steel, bare copper, tinned copper, silver coated copper, or nickel coated copper. The conductive wire 112 may be measured AWG #0000 to AWG #40. As used herein, "AWG" stands for American Wire Gauge. Gauges within the AWG standard measure a diameter of a wire to be between 0.46 inch to 0.0031 inch. The conductive wire 112 may be any suitable size, shape, or configuration.

In some embodiments, as depicted in FIG. 2, the conductive wire 112 is coupled to the spool 122 on one end by a fastener, adhesive, or other coupling mechanism. The conductive wire 112 includes the attachment mechanism 118 on one end opposite to where the wire is attached to the spool 122. In some instances, as depicted in FIGS. 1 and 2, the attachment mechanism 118 is a carabiner that is selectively attached to one or more external objects. The conductive wire 112 may be attached to the carabiner by being looped with a thimble and crimp about one end of the carabiner. The attachment mechanism 118 may be a variety of other attachments, including a hook-and-loop attachment mechanism, a magnet, or another type of fastener. In other instances, the attachment mechanism 118 is an apparatus that is configured to be permanently attached to a device. For example, in the field of weight lifting, the attachment mechanism 118 may be attached (e.g., via a hinge or the like) to a squat bar or other equipment. The attachment mechanism 118 may be attached to any object in which the user desires to know the movement of the object in three dimensions. One benefit to being permanently attached to another object is the movement tracking device 100 may be set a permanent position to always measure the intensity of movement, the direction of movement, and/or the movement history of the object. In some embodiments, the attachment mechanism 118 may be a straight gate, bent gate, wire gate, twist lock gate, or auto-locking gate carabiner.

The stopper 116 of the conductive wire 112, as seen in FIG. 2, is a polymeric ball. The polymeric ball may be silicone or polyurethane, for example. The stopper 116 may be a number of other shapes and materials that prevent the conductive wire from fully retracting within the housing 102 to where a user could not extract the wire therefrom. That is, the stopper 116 prevents the attachment mechanism 118 at the end of the conductive wire 112 from being retracted into the housing 102, which ensures that the user is able to readily access the attachment mechanism 118.

Resonators

In some embodiments, as depicted in FIGS. 4-8, a plurality of resonators 132 (i.e. inductive sensors and/or emitters) surrounds the conductive wire 112. In some instances, the resonators 132 comprise combined emitters and sensors. In other instances, the emitters and sensors may be partially or wholly separate components that cooperate to form the resonators 132. In some embodiments, three separate resonators 132 are disposed around the conductive wire 112. Any number of resonators may be used. In some instances, the resonators 132 are angled downward relative to the z-axis towards the conductive wire 112. As seen in FIG. 4, the plurality of resonators 132 are coupled to the PCB 134 by sensor wiring, and the PCB 134 includes etched triangular copper inductive coils. The plurality of resonators 132 are configured to detect metal, such as the conductive wire 112. For example, the plurality of resonators 132 form an induction loop where electric current passes through the plurality of resonators 132 to create one or more magnetic fields. For example, each emitter in the plurality of resonators 132 creates a single magnetic field. In some instances, when electricity passes through inductive coils contained within the resonators 132, the resonators 132 act as emitters. For example, the resonators 132 couple to a driver chip (not shown) and processor (not shown) where the driver chip switches the resonators 132 from outputting a magnetic field to receiving changes in the magnetic field. For example, the change in inductance may be measured as greater or less than a specified inductance. As a metal, e.g., the conductive wire 112, approaches the resonators 132, the current flowing through the loop increases as the metal approaches the inductive sensor. The change in current as the conductive metal approaches sends a signal back to the PCB 134 via wiring. The plurality of resonators 132 surrounding the conductive wire 112 allow for the processor on the PCB 134 to calculate the distance from each individual inductive sensor to, in turn, calculate the precise location of the conductive wire 112 within the three resonators 132 in the x and z axes. In some embodiments, the plurality of resonators 132 comprise two or more inductive sensors or emitters. The multiple inductive sensors and emitters may be embedded into one component that surrounds the conductive wire 112. For example, a ring shaped sensor may include two or more internal inductive sensors, or as seen in FIG. 4, multiple triangular shaped components may each contain an inductive sensor and an emitter. In some embodiments, the resonators 132 include inductive coils configured to directly measure the distance between a PCB 134 coil sensor and a mean distance of the conductive wire 112 that bisects an inductive field. With data from each of the three coils, a calibration table (not shown) is programmed within the processor to determine the distance of the conductive wire 112 at the surface of the aperture 110 to each of the resonators 132.

Figure 5:
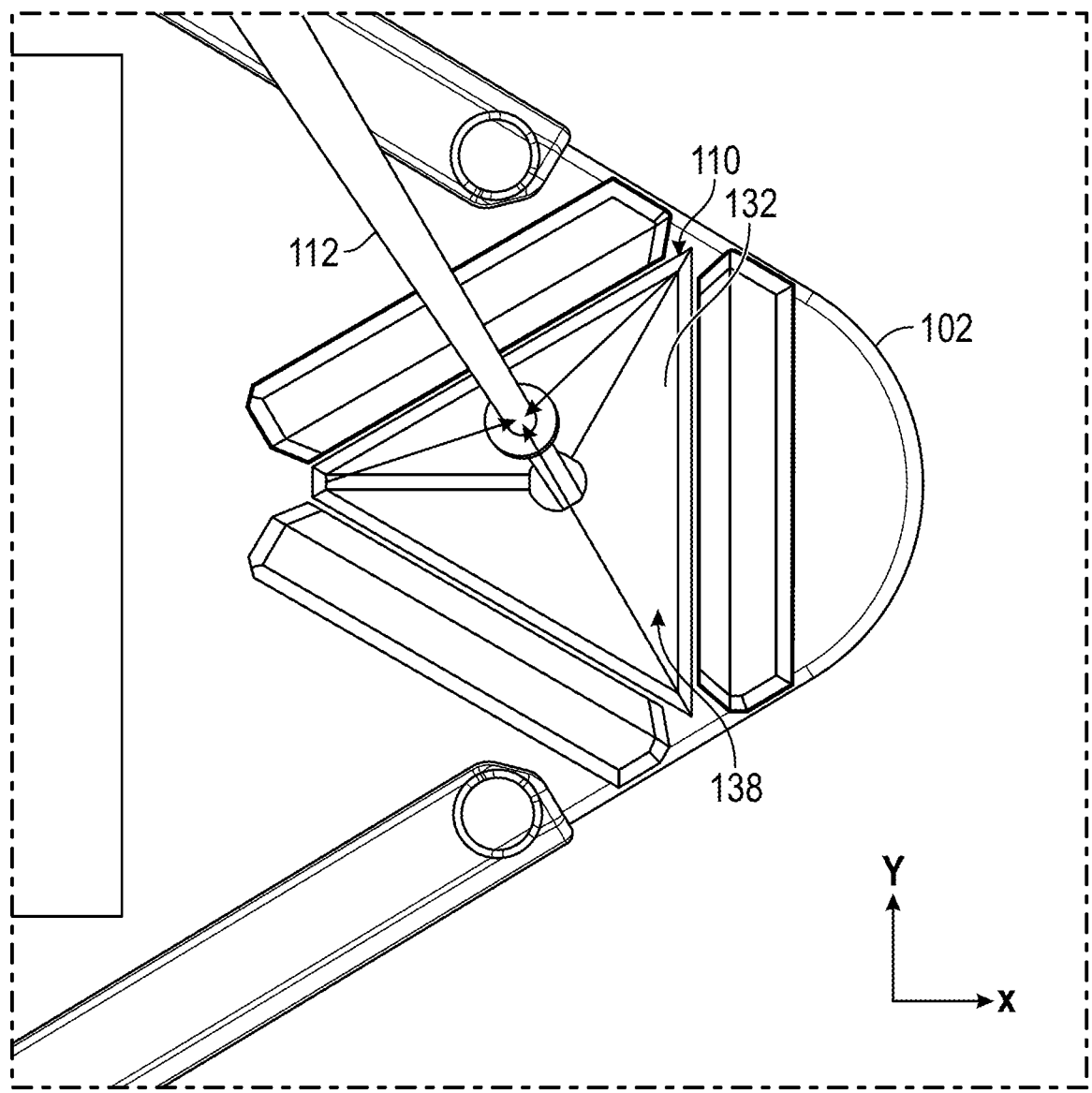
FIG. 5 is a top view of one embodiment of the plurality of resonators according to one or more embodiments of the disclosure.
Figure 6:
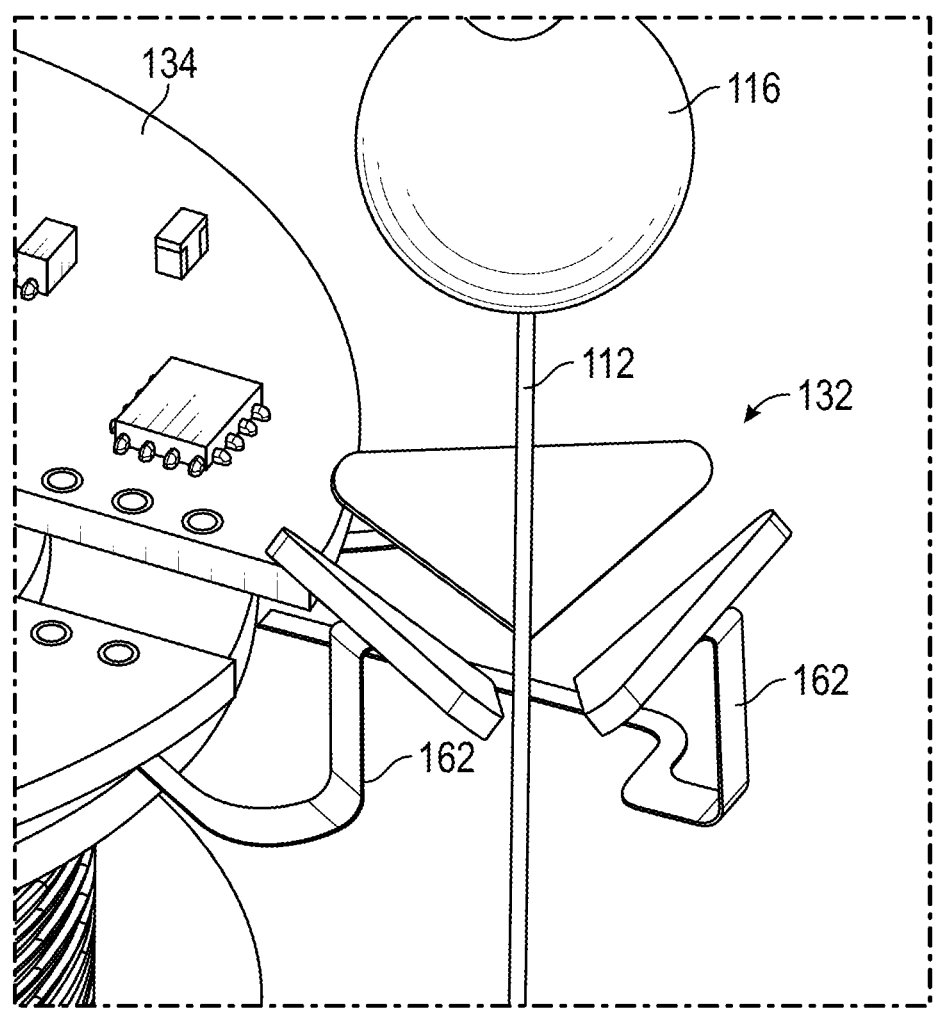
FIG. 6 is a perspective view of one embodiment of the plurality of resonators according to one or more embodiments of the disclosure.
Figure 7:
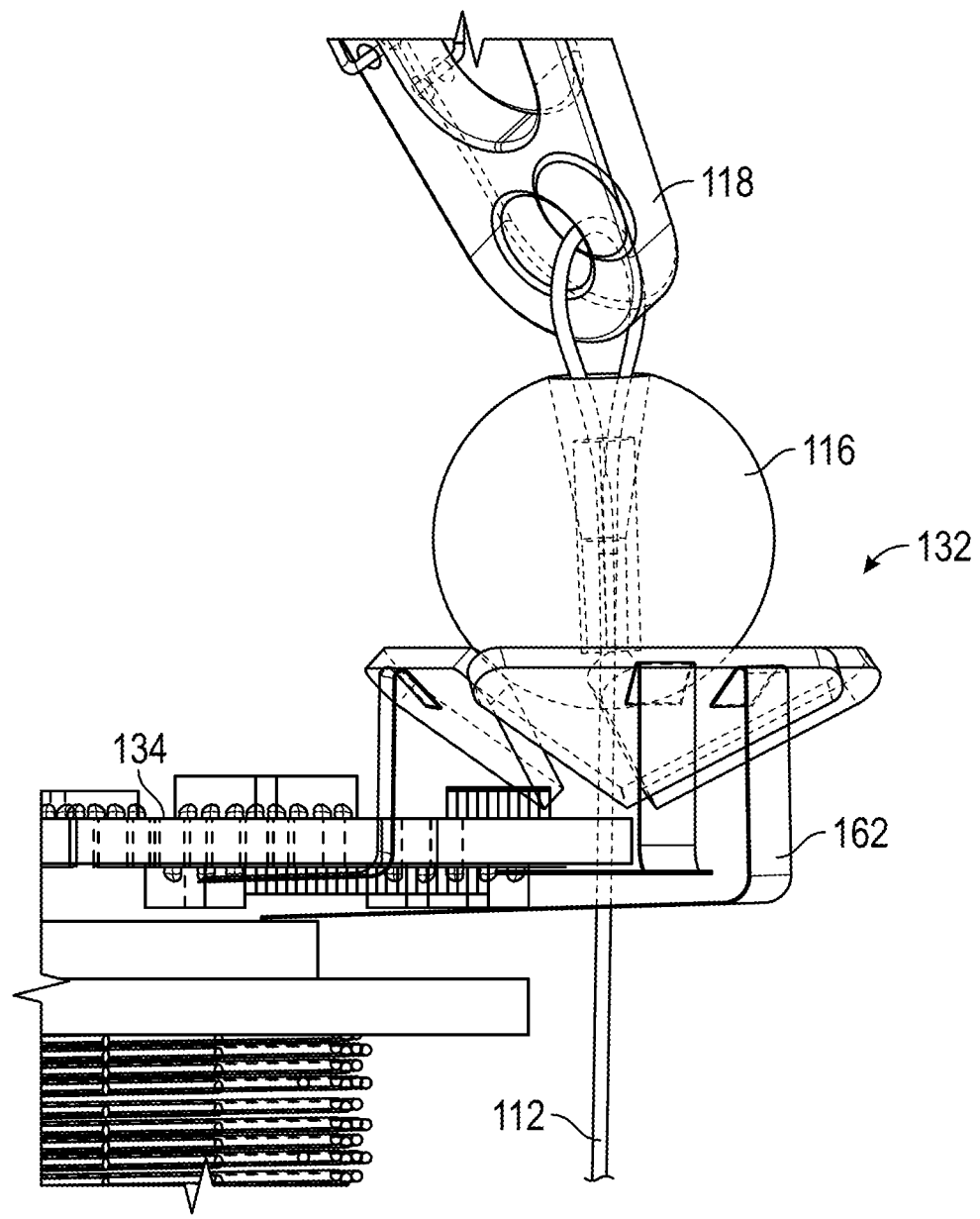
FIG. 7 is another perspective view of one embodiment of the plurality of resonators according to one or more embodiments of the disclosure.
Figure 8:
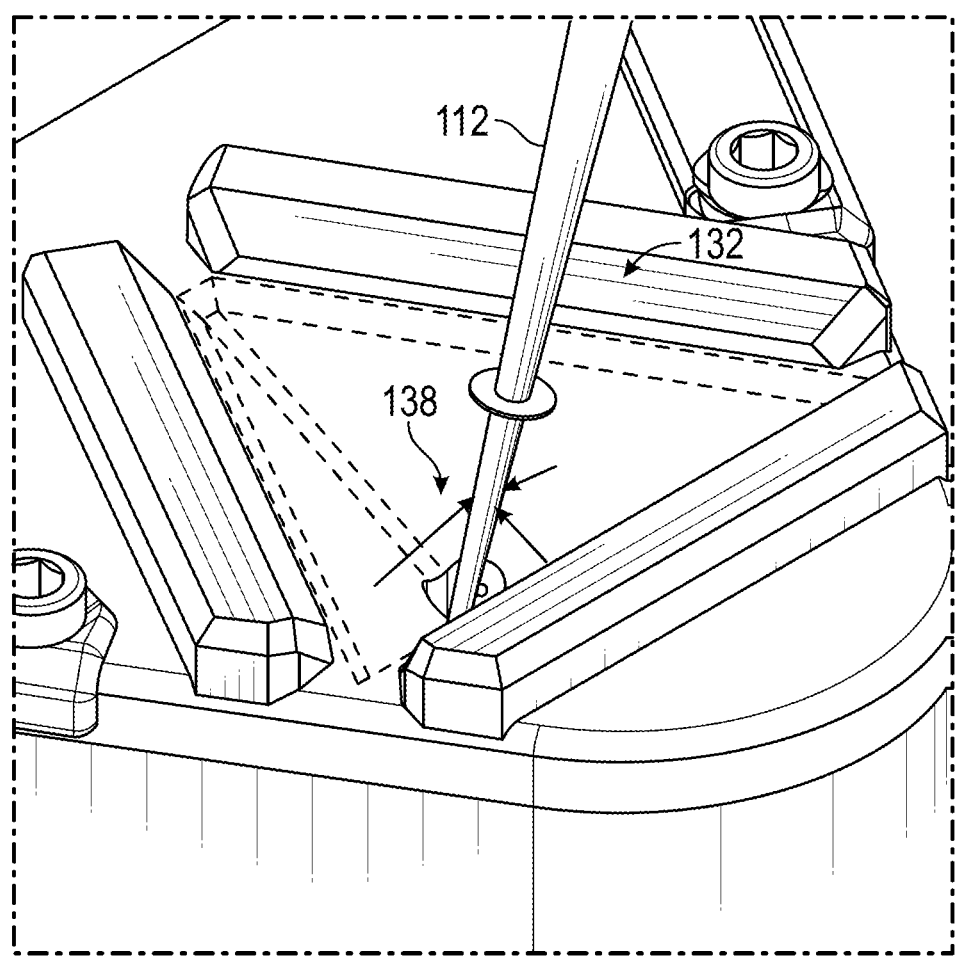
FIG. 8 is another perspective view of one embodiment of the plurality of resonators according to one or more embodiments of the disclosure.

In some embodiments, as seen in FIG. 5, the movement tracking device 100 includes three resonators 132 that are configured to create a magnetic field plane 138 to communicate with the processor the movement of the conductive wire 112 along the x-axis and y-axis. In some instances, the plurality of resonators 132 are parallel with the conductive wire 112 protruding from the device housing 102. That is, in some instances, the longitudinal axis of each of the resonators 132 are parallel to the longitudinal axis of the conductive wire 112. In other instances, the plurality of resonators 132 are perpendicular to the conductive wire 112. All or some of the plurality of resonators 132 may be tilted at an angle between perpendicular and parallel with the conductive wire 112. One benefit to tilting the plurality of resonators 132 away from a neutral position of the conductive wire 112 is to allow for a larger active measurement zone above the housing 102. The resonators 132, as seen in FIG. 7, have at least one arm 162 supporting each sensor. In some instances, the at least one arm 162 includes a flexible cable that provides electrical communication between the PCB 134 and the resonators 132. The arm 162 may be attached to the housing 102 or an internal structure thereof (e.g., the PCB 134). In other embodiments, the plurality of resonators 132 may include two resonators. The two resonators may be used in a spherical coordinate system to calculate an X angle and a Y angle. For example, the resonators may be configured perpendicularly to one another so that one does not bisect the other.

In some embodiments, a processor on the PCB 134 or a processor in communication therewith is in communication with the plurality of resonators 132. The PCB 134 may include multiple processors. Multiple processors may be configured to communicate and calculate simultaneous sensor inputs of two or more resonators, the switching of resonators from input to output, and the algorithms to convert inductance to digital data. The information is then translated and sent to a digital display located on the device itself or elsewhere, e.g., over a network.

The housing 102 may also contain a radio transceiver that transmits information to a wireless device (e.g., a wireless mobile device). The transmission may be by Bluetooth, WiFi, WiFi Direct, near-field communications (NFC), or another suitable wireless protocol. The transmission may also be via hardwire cable, such as fiber optic or Ethernet cable. The wireless mobile device may be a smartphone, tablet, wearable device, laptop, or other device. The mobile device communicates data with the movement tracking device 100, such as movement data, the power of an internal battery data, the strength of the wireless signal, and various other data. The data received by the mobile device displays for a user on a liquid-crystal display (LCD) screen, or to an LED display. The wireless mobile device may include a radio, a source of power, a display, a memory, and a processor. Each piece of data may be displayed by an application executed, for example, by a wireless mobile device that received the data from the movement tracking device 100. The wireless signal generated by the movement tracking device 100 is received by the radio of the wireless mobile device, and then sent via electric circuits to a processor within the wireless mobile device. The processor then transmits the information to memory, a remote server, and/or the display. The display then presents visual information to a user. For example, the display may show the intensity or total movement of the conductive wire 112 of the movement tracking device 100.

In some embodiments, the plurality of resonators 132 may be etched inductive coils, chip inductors, wire inductors, radio-frequency identification (RFID), or any other alternating current magnetic field inducing component. The resonators may be a general sensor or a nonferrous metal sensor. Optional inductive shielding to prevent parasitic inductance, inductive interference, electromagnetic interference, or any other interference that can disturb the precise reading of the resonators may be present.

Figure 9:
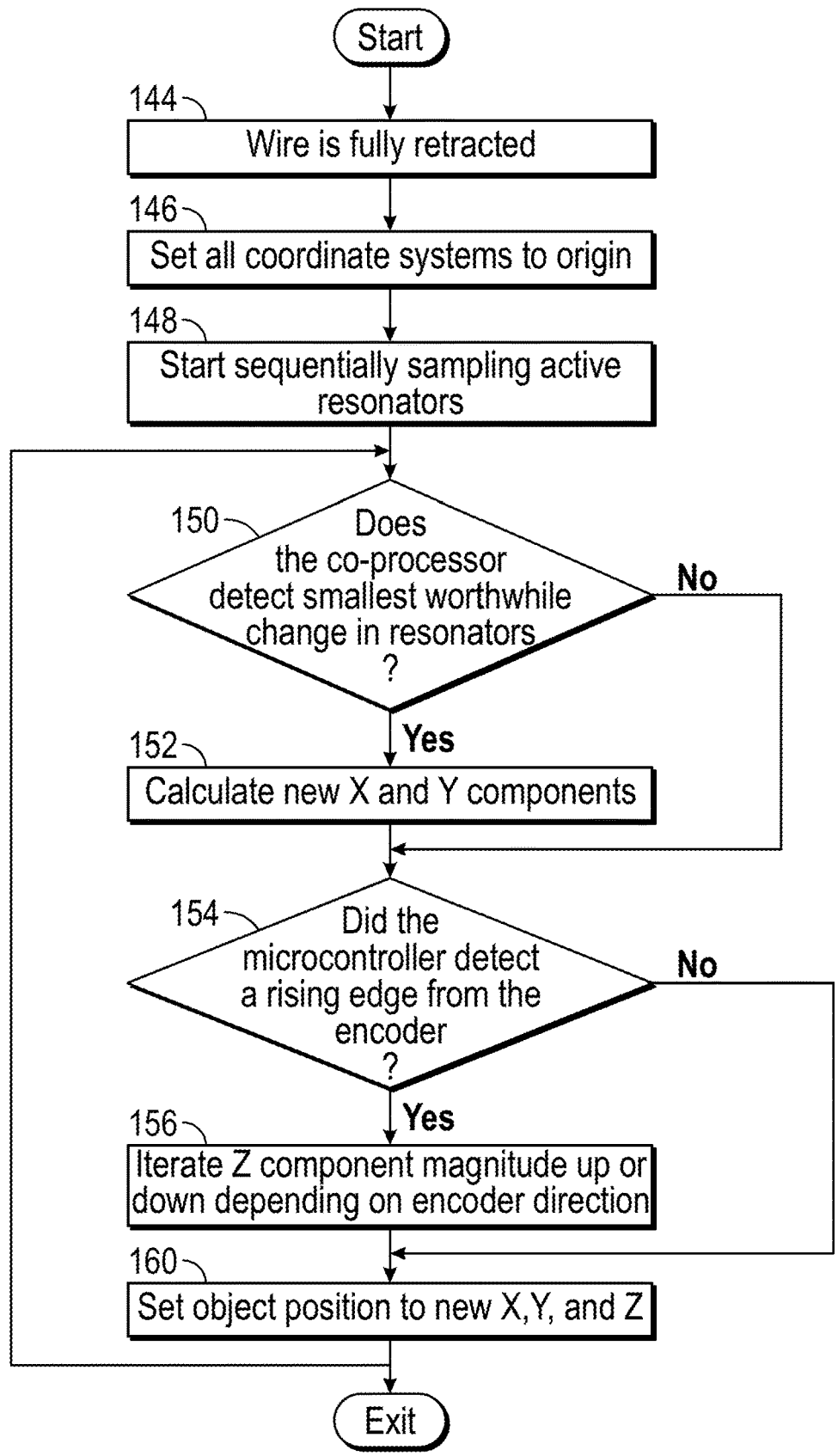
FIG. 9 is a flow chart detailing one embodiment of a tracking algorithm according to one or more embodiments of the disclosure.

FIG. 9 illustrates one embodiment of a methodology for measuring the movement of the conductive wire 112 as described herein. First, the conductive wire is fully retracted 144 from the housing 102. The coordinate systems will then be set to origin 146 by the processor on the PCB 134. The resonators 132 (e.g., active resonators) then start sequentially sampling. Instructions loaded onto the processor then execute instructions to determine whether a preset change in distance of the conductive wire 112 should correspond to a change 150 in the resonators 132. The preset change in distance may be limited, such as movement of less than a millimeter, to a larger distance, such as greater than a millimeter. If the processor determines the preset change is worth the change in resonators 132, the process will then execute instructions to calculate a new x and y component 152 of the conductive wire 112. After the processor determines whether the preset change is worth a change in resonators 132, the processor will then determine whether the encoder system 120 measured a change in the conductive wire 112 being pulled from the spool 122. If the encoder system 120 communicates a change, then the processor iterates a change in the z-axis measurement 156. If no change has occurred for the encoder system 120 or after the z-axis measurement is calculated, then the processors sets the object position to a new x-axis, y-axis, and z-axis 160. The process repeats after sequential sampling of the resonators 132 until the movement tracking device 100 is powered down.

Algorithms

The displacement of the conductive wire 112 is determined by one or more algorithms. For example, sensor fusion finds three-dimensional spatial position of the end of the conductive wire 112 by calculating the angles of the vector relative to the base coordinate system. The calculation may then factor in the z-axis displacement to calculate the vector magnitude. A polar coordinate system, for example, uses one or more coils combined with z-axis displacement to calculate the two dimensional position of an object. The plurality of resonators may measure the angle of the vector, and the vector magnitude may then be determined by z-axis displacement. Another method, sphere-sphere-circle-sphere system, uses two or more resonators in the plurality of resonators. The resonators combined with z-axis displacement calculate three-dimensional position of an object. Each resonator is used to measure the angle of the vector, and the vector magnitude may then be determined by z-axis displacement. The sphere-sphere-circle-sphere system relies on the relationship between one resonator and the conductive wire that is modeled as a sphere around the centroid of the resonator. The radius of this model is the sensed distance to the target, and the target may be at any location on the surface of the sphere. The second resonator is used to constrain the potential locations of the target to a circle drawn by an intersection of the sphere from the first resonator and the sphere from the second resonator. A third resonator in the sphere-sphere-circle-sphere system may be used to locate the single point on the intersection circle that the target exists.

Another system, the Barycentric coordinate system, includes at least three resonators. The three resonators combined with z-axis displacement and calculate a three dimensional position of an object. Within the Barycentric system, a calibration is required such that the perpendicular distance sensed between the centroid of the resonator and the target may be mapped to a point on a triangle between the top surfaces of the three resonators. Once each resonator value is mapped to a point on the triangle, a Barycentric coordinate system may be used to locate a unique position of the conductive wire.

Although specific embodiments of the disclosure have been described, other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

I claim:

1. A movement tracking device for monitoring movement of exercise equipment, the movement tracking device comprising:
    a housing;
    a rotatable spool secured within the housing;
    a rotary sensor in operable communication with the spool;
    a conductive wire configured to be unspooled from and respooled onto the rotatable spool, wherein the conductive wire has a distal end extendable from the housing and is configured to be attached to the exercise equipment;
    a plurality of resonators disposed in or on the housing and positioned about the conductive wire, wherein each of the plurality of resonators are configured to create one or more magnetic fields through which the conductive wire extends; and
    a processor in communication with the plurality of resonators and the rotary sensor, wherein the processor is configured to receive information from the plurality of resonators and the rotary sensor and determine a position of the conductive wire.

2. The movement tracking device of claim 1, wherein the rotary sensor comprises an encoder system which comprises an encoder and an encoder wheel configured to rotate with the spool.

3. The movement tracking device of claim 2, wherein the encoder system is configured to rotate within the housing at the same rate the conductive wire is pulled from the spool.

4. The movement tracking device of claim 1, further comprising a retractable mechanism coupled to the spool, wherein the retractable mechanism is configured to rotate the spool back to a starting position.

5. The movement tracking device of claim 4, wherein the conductive wire comprises a first position, wherein the conductive wire is fully retracted within the device housing when in the first position and configured to be extended therefrom, wherein when the conductive wire extends from the first position, the spool and the rotary sensor rotate at the same rate the conductive wire is pulled.

6. The movement tracking device of claim 1, wherein:
    the conductive wire comprises a proximal end coupled to the spool;
    an attachment mechanism is coupled to the distal end of the conductive wire; and
    a stopper is coupled to the conductive wire and configured to prevent the attachment mechanism from fully retracting within the housing.

7. The movement tracking device of claim 1, wherein the plurality of resonators are configured to send information to the processor as the conductive wire passes through the one or more magnetic fields.

8. The movement tracking device of claim 1, further comprising a display coupled to the housing in communication with the processor, wherein the display is configured to present information received by the processor.

9. The movement tracking device of claim 1, wherein the device housing comprises at least one bumper configured to reduce vibration resonating through the device housing.

10. The movement tracking device of claim 1, wherein the housing further comprising an aperture and the conductive wire extends from the spool through the aperture.

11. A movement tracking device for monitoring movement of exercise equipment, the movement tracking device comprising:
   a housing;
   a spool stored within the housing, the spool comprising a starting position, wherein the spool is configured to rotate back to the starting position when rotated away from the starting position;
   an encoder system coupled to the spool and configured to measure rotation of the spool;
   a conductive wire wrapped about the spool, wherein the conductive wire is configured to selectively extend out of the housing and be attached to the exercise equipment; and
   a plurality of resonators mounted within the housing, wherein the plurality of resonators are configured to sense movement of the conductive wire.

12. The movement tracking device of claim 11, further comprising a processor in communication with the plurality of resonators and encoder system, wherein the processor is configured to execute instructions that, in response to execution, cause the processor to receive information form the plurality of resonators and the encoder system to calculate a position of the conductive wire.

13. The movement tracking device of claim 11, further comprising a display coupled to the housing in communication with the processor, wherein the display is configured to present information received by the processor.

14. The movement tracking device of claim 11, further comprising a retractable mechanism coupled to the spool, wherein the retractable mechanism is configured to rotate the spool to the starting position.

15. The movement tracking device of claim 11, further comprising:
   an attachment mechanism configured to be attached to exercise equipment coupled to the conductive wire on a first end of the conductive wire opposite a second end of the conductive wire, wherein the second end of the conductive wire is coupled to the spool; and
   a stopper configured to prevent the conductive wire from fully retracting within the housing.

16. The movement tracking device of claim 11, wherein the housing comprises one or more bumpers configured to absorb shock forces applied to the housing.

17. The movement tracking device of claim 11, further comprising,
   a power source coupled within the housing;
   a power button configured to operate the power source; and
   a charging port coupled to the housing and configured to accept power for the power source.

* * * * *